(12) United States Patent
Hodges et al.

(10) Patent No.: US 7,335,292 B2
(45) Date of Patent: *Feb. 26, 2008

(54) SENSOR WITH IMPROVED SHELF LIFE

(75) Inventors: Alastair McIndoe Hodges, Blackburn South (AU); Ronald Chatelier, Bayswater (AU)

(73) Assignee: LifeScan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/630,441

(22) Filed: Jul. 29, 2003

(65) Prior Publication Data

US 2004/0069657 A1 Apr. 15, 2004

Related U.S. Application Data

(63) Continuation of application No. 09/664,688, filed on Sep. 19, 2000, now Pat. No. 6,652,734, which is a continuation of application No. PCT/AU99/00166, filed on Mar. 16, 1999.

(30) Foreign Application Priority Data

Mar. 20, 1998 (AU) ..................................... PP2503

(51) Int. Cl.
*G01N 27/30* (2006.01)
(52) U.S. Cl. ................. 205/775; 204/400; 204/290.11; 427/2.11
(58) Field of Classification Search ............... 204/400, 204/403.01, 280, 290.01, 290.11; 205/775; 427/2.11
See application file for complete search history.

(56) References Cited

U.S. PATENT DOCUMENTS

| | | |
|---|---|---|
| 3,616,411 A | 10/1971 | Rudek |
| 4,053,381 A | 10/1977 | Hamblen et al. |
| 4,224,125 A | 9/1980 | Nakamura et al. |
| 4,259,165 A | 3/1981 | Miyake |
| 4,301,412 A | 11/1981 | Hill et al. |
| 4,303,887 A | 12/1981 | Hill et al. |
| 4,374,013 A | 2/1983 | Enfors |
| 4,404,066 A | 9/1983 | Johnson |
| 4,431,004 A | 2/1984 | Bessman et al. |
| 4,431,507 A | 2/1984 | Nankai et al. |
| 4,517,291 A | 5/1985 | Seago |
| 4,533,440 A | 8/1985 | Kim |
| 4,545,382 A | 10/1985 | Higgins et al. |
| 4,664,119 A | 5/1987 | Bessman et al. |
| 4,711,245 A | 12/1987 | Higgins et al. |
| 4,790,925 A | 12/1988 | Miller et al. |
| 4,897,173 A | 1/1990 | Nankai et al. |
| 4,900,424 A | 2/1990 | Birth et al. |
| 4,963,815 A | 10/1990 | Hafeman |
| 4,988,429 A | 1/1991 | Matthiessen |
| 5,064,516 A | 11/1991 | Rupich |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,185,256 A | 2/1993 | Nankai et al. |
| 5,192,415 A | 3/1993 | Yoshioka et al. |
| 5,229,282 A | 7/1993 | Yoshioka et al. |
| 5,264,103 A | 11/1993 | Yoshioka et al. |
| 5,272,087 A | 12/1993 | El Murr et al. |
| 5,312,590 A | 5/1994 | Gunasingham |
| 5,314,605 A | 5/1994 | Matthiessen |
| 5,320,732 A | 6/1994 | Nankai et al. |
| 5,382,346 A | 1/1995 | Uenoyama et al. |
| 5,384,028 A | 1/1995 | Ito |
| 5,385,846 A | 1/1995 | Kuhn et al. |
| 5,393,399 A | 2/1995 | Van den Berg et al. |
| 5,413,690 A | 5/1995 | Kost et al. |
| 5,437,999 A | 8/1995 | Diebold et al. |
| 5,508,171 A | 4/1996 | Walling et al. |
| 5,509,410 A | 4/1996 | Hill et al. |
| 5,520,787 A | 5/1996 | Hanagan et al. |
| 5,527,446 A | 6/1996 | Kosek et al. |
| 5,529,676 A * | 6/1996 | Maley et al. ............... 204/409 |
| 5,552,840 A | 9/1996 | Ishii et al. |

(Continued)

FOREIGN PATENT DOCUMENTS

AU  B-69245/91  7/1991

(Continued)

OTHER PUBLICATIONS

Allen et al, J. Electroanal. Chem., 178 (1984), pp. 69-86.*

(Continued)

*Primary Examiner*—Kaj K. Olsen
(74) *Attorney, Agent, or Firm*—Nutter, McClennen & Fish, LLP

(57) ABSTRACT

The present invention provides a metal electrode stabilized by a coating, the coating comprising a sulfur containing moiety in its molecular structure. The coating may also include a hydrophilic group and a spacer between the sulfur containing moiety and the hydrophilic group. Preferably, the sulphur-containing moiety is selected from the group comprising thiol, disulphide and SOx, and the hydrophilic group is selected from the group comprising hydroxyl, amine, carboxyl, carbonyl, oligo (ethylene oxide) chain, and zwitterionic species. Compounds useful in the present invention include 2-mercaptoethanol, 2-mercaptoethylamine, 3-mercaptopropionic acid, thiophene, 4-carboxythiophene, cysteine, homocysteine, and cystine.

15 Claims, No Drawings

U.S. PATENT DOCUMENTS

| | | | |
|---|---|---|---|
| 5,567,302 | A | 10/1996 | Song et al. |
| 5,628,890 | A | 5/1997 | Carter et al. |
| 5,645,709 | A | 7/1997 | Birch et al. |
| 5,863,400 | A | 1/1999 | Drummond et al. |
| 5,942,102 | A | 8/1999 | Hodges et al. |
| 5,997,817 | A | 12/1999 | Crismore et al. |

FOREIGN PATENT DOCUMENTS

| | | |
|---|---|---|
| AU | A-31042/93 | 7/1993 |
| AU | A-54873/94 | 8/1994 |
| DE | 43 12 126 A1 | 10/1994 |
| EP | 0 125 137 A2 | 11/1984 |
| EP | 0 251 915 A2 | 1/1988 |
| EP | 0 255 291 A1 | 2/1988 |
| EP | 0 278 647 A2 | 8/1988 |
| EP | 0 299 779 A2 | 1/1989 |
| EP | 0 351 516 A2 | 1/1990 |
| EP | 0 170 375 B1 | 5/1990 |
| EP | 0 400 918 A1 | 12/1990 |
| EP | 0 560 336 A1 | 3/1993 |
| EP | 0 609 760 A1 | 1/1994 |
| EP | 0 585 933 A2 | 3/1994 |
| EP | 0 698 787 A1 | 2/1996 |
| EP | 0 127 958 B2 | 4/1996 |
| EP | 0 459 782 B1 | 8/1996 |
| EP | 0699 901 A1 | 3/1999 |
| GB | 2 069 702 A | 8/1981 |
| GB | 2 201 248 A | 8/1988 |
| GB | 2 215 846 | 9/1989 |
| JP | 6-34600 | 2/1994 |
| WO | WO 89/08713 | 9/1989 |
| WO | WO 91/09304 | 6/1991 |
| WO | WO 94/02842 | 2/1994 |
| WO | WO 95/16198 | 6/1995 |
| WO | WO 95/21934 | 8/1995 |
| WO | WO 95/28634 | 10/1995 |
| WO | WO 97/00441 | 1/1997 |
| WO | WO 97/01092 | 1/1997 |
| WO | WO 97/43274 | 11/1997 |
| WO | WO-97/45720 | 12/1997 |
| WO | WO 98/11426 | 3/1998 |
| WO | WO 98/43074 | 10/1998 |

OTHER PUBLICATIONS

Schlereth et al, Electroanalysis, 7(1) (1995), pp. 46-54.*
French et al, Langmuir, 1998, 14, pp. 2129-2133.*
CAPLUS abstract for Schweiss et al, Materials Science Forum (1998), pp. 287-288.*
Dong et al, Bioelectrochemistry and Bioenergetics 42 (1997), pp. 7-13.*
Schweiss et al, Materials Science Forum, vol. 287-288, pp. 427-430, 1998.*
Sun Hao and Wang Hongen, "Glucose Oxidase Immobilized on Thiol/Gold Self-assembled Film and Use Thereof" (Department of Biology, Northeast Normal University) pp. 1-8, journal and date unknown.
Kajiya, et al., Chemistry Letters, pp. 2107-2110, 1993.
Pandey, et al., Biosensors and Bioelectronics, vol. 10(8), 1995.
McRipley, et al., Journal of ElectroAnalytical Chemistry, vol. 414(2), pp. 235 to 246, 1996.
Mann-Baxbaum, et al., Sensors and Actuators, vol. B1(16), 1990, pp. 518 to 522.
Derwent Abstract Accession No. 90/271278/36, JP 02 190754 A to Canon KK, Jul. 26, 1990.
Derwent Abstract Accession No. 90-136589/18, JP 02 085755 A to Teijin KK, Mar. 17, 1990.
PCT International Search Report for PCT/AU 99/00166, date unknown.
Mizutani, et al., Analytica Chimica Acta 364 (1998) 173-179.
He, et al., Talanta 44 (1997) pp. 885-890.
Dong, et al., Bioelectrochemistry and Bioenergetics 42 (1997) 7-13.
Hubbard, et al. "The Theory and Practice of Electrochemistry with Thin Layer Cells", Electroanalytical Chemistry; New York, 1970, vol. 4, pp. 129-214.
Anderson, et al. "Thin-Layer Electrochemistry: Steady-State Methods of Studying Rate Processes"; Journal of Analytical Chemistry; 1965; pp. 295-303.
Patent Abstract for JP 3-167464 (A), issued Jul. 19, 1991; Application No. 64-304806, filed Nov. 27, 1989; "Humidity-Sensitive Element and It's Manufacture".
Patent Abstract for JP 59-3345 (A), issued Jan. 10, 1984; Application No. 57-111695, filed Jun. 30, 1982; "Dissolved Oxygen Meter Equipped with Electrode for Removing Interfering Component".
Ulman, A., "Formation and Structure of Self-Assembled Monlayers", Chemical Reviews, vol. 96, 1996, pp. 1533-1554.
Mirsky, V. M. et al., "Capacitive Monitoring of Protein Immobilization and Antigen Antibody Reactions on Monomolecular Alkythiol Films on Gold Electrodes", Biosensors & Bioelectronics, Elsevier Science Publishers, Barking, GB, vol. 12, No. 9/10, 1997, pp. 977-989.
Knichel, M. et al., "Utilization of a Self-Assembled Peptide Monolayer for an Impedimetric Immunosensor", Sensors and Actuators B, Elsevier Sequoia S.A., Lausanne, CH, voll. 28, No. 21 Aug. 1, 1995, pp. 85-94.

* cited by examiner

SENSOR WITH IMPROVED SHELF LIFE

RELATED APPLICATIONS

This application is a continuation of application Ser. No. 09/664,688, filed Sep. 19, 2000, now U.S. Pat. No. 6,652,734 which is a continuation, under 35 U.S.C. § 120, of PCT International Application No. PCT/AU99/00166, which has an International filing date of Mar. 16, 1999, which designated the United States of America, which was published by the International Bureau in English on Sep. 30, 1999, and which claims the benefit of Australian Provisional Application No. PP 2503 filed on Mar. 20, 1998.

TECHNICAL FIELD

The invention relates to apparatus comprising one or more metal electrodes such as electrochemical cells, sensor elements and the like, and more particularly to extending the shelf life of such apparatus.

BACKGROUND ART

Metal electrodes have proved useful in sensor elements for sensing a diverse range of biologically important molecules eg glucose, and for determining physical properties such as pH. A range of possible configurations and applications involving metal electrodes are discussed in our co-pending applications PCT/AU96/00210, PCT/AU96/00365 and PCT/AU96/00723.

A desirable attribute of all sensor elements is that they have a long shelf life—that is, the sensing characteristic of the sensor element does not change significantly between manufacture and use (ie on storage).

In an electrochemical sensor element the stability of the electrode is critical to the stability of the sensor as a whole. Typically, when left to stand for long periods of time, electrodes become prone to instability in subsequent use thus limiting the useful shelf life. It is thought that such instability is caused by absorption or reaction of the metallic surface with atmospheric contaminants. It has also been observed that filling time of sensors deteriorates on prolonged storage.

It is an object of the present invention to overcome or ameliorate at least some of the above disadvantages in the prior art.

Surprisingly, the present applicant has found that by coating a metal electrode with a monolayer or multilayer of selected materials, electrode behavior can be significantly stabilised in comparison with uncoated metal electrodes without loss of the desirable sensing characteristics of the electrodes.

DESCRIPTION OF THE INVENTION

According to a first aspect, the invention consists in a metal electrode stabilised by a coating, said coating comprising a sulfur containing moiety in its molecular structure, said coating increasing the temporal stability of the electrode relative to a corresponding uncoated metal electrode without modifying other electrochemical properties of said metal electrode.

"Comprising" as herein used is used in an inclusive sense, that is to say in the sense of but not limited to "including" or "containing". The term is not intended in an exclusive sense ("consisting of" or "composed of").

Preferably, the sulphur-containing moiety is selected from the group comprising thiol, disulphide and $SO_x$. Most preferably the sulphur-containing moiety is a disulphide. The sulphur-containing moiety may also be incorporated in a cyclic structure.

According to a second aspect, the invention consists in a metal electrode stabilised by a coating according to the first aspect, further comprising a hydrophilic group in its molecular structure.

Preferably, the hydrophilic group is selected from the group comprising hydroxyl, amine, carboxyl, carbonyl, oligo (ethylene oxide) chain, and zwitterionic species. Most preferably, the hydrophilic group is a zwitterionic species. The most preferred zwitterionic species comprises an amine and a carboxyl group in proximity.

According to a third aspect, the invention consists in a metal electrode stabilised by a coating according to the second aspect, further comprising a spacer between the sulphur-containing moiety and the hydrophilic group.

Preferably, in the third aspect, the spacer consists of an alkyl group or an aromatic group. It is preferable that methylene or ethylene groups be included in the spacer element.

According to a fourth aspect, the invention consists in a method of preparing a metal electrode stabilised by a coating, comprising the step of contacting a metal electrode with a substance comprising a sulphur-containing moiety in its molecular structure.

According to a fifth aspect, the invention consists in a method of preparing a metal electrode stabilised by a coating, comprising the steps of contacting a metal electrode with a substance comprising a sulphur-containing moiety and a hydrophilic group in its molecular structure.

According to a sixth aspect, the invention consists in a method of preparing a metal electrode stabilised by a coating comprising the steps of contacting a metal electrode with a substance comprising a sulphur-containing moiety, a hydrophilic group and a spacer between the sulphur-containing moiety and the hydrophilic group in its molecular structure.

The preferred substances for use in the methods described in the fourth, fifth and sixth aspects are identical to those substances described in respect of the first, second and third aspects.

The invention also consists in a method of sensing an analyte, comprising the step of substituting the electrode in a known sensor device with a metal electrode stabilised by a coating according to the present invention, and sensing an analyte.

BEST MODE FOR CARRYING OUT THE INVENTION

Various embodiments of the invention will now be described by way of example only.

It is known in the prior art that thiols form coatings on metals. Thiols have also been used to tether species such as antibodies onto metal surfaces, for instance those of gold particles, for the purposes of immobilisation etc. One would expect that such coatings would also bind contaminants to the surface.

As much electrode chemistry involves interaction at the electrode surface, it is thus surprising that coatings used to bind molecules to the metal surface can be useful in preventing contamination of the electrode surface. It is also surprising that notwithstanding the application of the coating an electrode retains desirable electrochemical properties. The procedure for preparing the metal electrode stabilised by a coating involves contacting a metal electrode with selected sulphur-containing compounds, such as thiols, disulphides and compounds of the formula $SO_x$ among others being suitable in the context of the present invention. The coatings also desirably contain a hydrophilic group which includes such species as hydroxyl, amino, carboxyl, carbonyl, oligo (ethylene oxide) chains and zwitterionic species. The latter two compounds indicate that compounds having one or more hydrophilic groups are also suitable groups for use in the present invention.

Between the sulphur group, which acts to tether the molecule onto the metal surface, and the hydrophilic group, which presents a hydrophilic surface, spacers may be employed.

Compounds useful in the present invention include, but are not limited to 2-mercaptoethanol, 2-mercaptoethylamine, 3-mercaptopropionic acid, thiophene, 4-carboxy thiophene, cysteine, homocysteine and cystine. Most preferably the molecule is cystine. In any of the above aspects, the D or L isomers can be used or mixtures of D and L isomers can be used, where such isomers are possible.

The compound in accordance with the invention is then applied as a monolayer or multilayer onto the surface of the electrode. It is possible to apply the compound by simply exposing the electrode to the coating material, with the coating material in either the vapour phase or in solution. The substance can be applied by dipping, spraying, painting, printing etc. After application, it is possible to wash the surface of the contacted electrode.

In a further aspect of the current invention the layer of the sulfur containing compound can optionally be overcoated with a surfactant layer. The surfactant layer can be applied after the application of the sulfur containing layer or at the same time as the sulfur containing layer, for example the sulfur containing species and the surfactant can be placed in a coating bath into which the electrode material is immersed. Due to the higher affinity of the sulfur containing species for the electrode material it will bind to the electrode surface in preference to the surfactant, leaving the surfactant in a layer over the sulfur containing layer An example of a suitable surfactant is Triton X-100.

EXAMPLES

Example 1

Preparation

The electrode coatings were applied to gold or palladium electrodes by immersing the sheet of material from which the electrodes were made into a 1 mM aqueous solution of the coating compound adjusted to pH 12 by the addition of potassium hydroxide. The contact time between the electrode material and the coating bath was typically 30 seconds. After coating, the electrodes were washed by immersion in a bath of water. In some cases, the electrodes were immersed in a third bath containing 1,000 ppm of triton X-100 in water. Finally, the electrode material sheets were dried by blowing with air at room temperature.

Example 2

Storage

The data in Tables 1 and 2 below show the effect on the electrode stability of coating the electrodes with sulphur-containing compounds. The stability was assessed using an accelerated test. The glucose sensors using coated or uncoated electrodes were stored either at 4° C. in the refrigerator ("fridge" ) or at 56° C. in an oven for two weeks. The sensors stored at 4° C. do not change significantly from their performance when freshly prepared and tested. Those stored in the oven are subject to accelerated ageing, which simulates longer ageing times at room temperature.

Example 3

Testings

After two weeks the sensors were tested with whole blood samples with various glucose concentrations, from about 3 mM to 30 mM. The background ferrocyanide concentration was measured (the reading obtained when a sample contains no glucose) and the overall precision and fill speed of the sensors was assessed. The effect of the electrode coatings is shown in Table 1. The fill speeds in Table 1 were assessed qualitatively by eye. The fill speeds in Table 2 were assessed quantitatively by videoing the filling of the sensor with a blood sample using an on-screen timer and subsequently determining the number of seconds required for the blood to fill each sensor.

It can be seen from the first pair of results, for a non-coated electrode, that artificial ageing dramatically increased the % cv (corresponding to decreased precision).

In contrast, for the last two pairs of results, the % cv's for the treated electrodes after artificial ageing were comparable to the % cv's of untreated electrodes on fridge storage and significantly better than accelerated aged untreated electrodes.

A desirable side effect of the present invention also appears to be maintenance of good fill speed for sensors on ageing.

TABLE 1

TEST DATA

| STORAGE | COATING | BACKGROUND (mM ferrocyanide) | MEAN % cv | FILL SPEED |
|---|---|---|---|---|
| Fridge | None | 1.01 | 3.8 | OK |
| Oven | None | 5.12 | 10.05 | very slow |
| Fridge | Cysteine | 1.3 | 4.5 | OK |
| Oven | Cysteine | 5.0 | 8.0 | slow |
| Fridge | Cysteine/trit | 1.98 | 3.1 | fast |
| Oven | Cysteine/trit | 2.17 | 5.4 | OK |
| Fridge | Homocysteine/trit | 1.02 | 4.6 | OK |
| Oven | Homocysteine/trit | 2.34 | 4.2 | faster than Cysteine/trit |
| Fridge | Cystine/trit | 0.63* | 4.1 | fast |
| Oven | Cystine/trit | 1.24* | 4.4 | good |

*saline rather than blood used to assess the background
Trit denotes an overcoating of Triton X-100.

TABLE 2

PRECISE FILL TIMES

| STORAGE | COATING | FILL TIME (secs) |
|---|---|---|
| Fridge | none | 1.0 |
| Oven | none | 5.3 |
| Fridge | Cystine | 0.4 |
| Oven | Cystine | 4.0 |
| Fridge | Cystine/trit | 0.3 |
| Oven | Cystine/trit | 1.4 |

A person skilled in the art will appreciate that the application process is very simple and facile and could be accomplished from the teaching hereof in many ways.

What is claimed is:

1. A coated metal electrode, the metal electrode comprising a coating and an overcoating, wherein the overcoating comprises a surfactant, wherein the coating comprises a sulfur containing moiety in its molecular structure, wherein
   the coating does not result in a loss of the sensing characteristics of the electrode, and wherein;
   the coating is selected from the group consisting of 2-mercaptoethanol, 2-mercaptoethylamine, thiophene, L-cysteine, L-cystine, D-cysteine, D-cystine, L-homocysteine, D-homocysteine, and wherein;
   a temporal stability of the coated metal electrode is greater than a temporal stability of a corresponding uncoated metal electrode.

2. The coated metal electrode according to claim 1, wherein the compound is a stereospecific compound.

3. The coated metal electrode according to claim 2, wherein the stereospecific compound comprises a mixture of D isomers and L isomers.

4. The coated metal electrode according to claim 2, wherein the stereospecific compound comprises a D isomer.

5. The coated metal electrode according to claim 2, wherein the stereospecific compound comprises an L isomer.

6. A method of preparing a metal electrode stabilized by a coating, the method comprising: contacting a metal electrode with a substance comprising a sulfur containing moiety in its molecular structure; and thereafter contacting the metal electrode with a surfactant, whereby a coated metal electrode is obtained, wherein
   the coating does not result in a loss of the sensing characteristics of the electrode, and wherein;
   the coating is selected from the group consisting of 2-mercaptoethanol, 2-mercaptoethylamine, 3-mercaptopropionic acid, thiophene, L-cysteine, L-cystine, D-cysteine, D-cystine, L-homocysteine, D-homocysteine, and wherein
   a temporal stability of the coated metal electrode is increased relative to that of a corresponding uncoated metal electrode.

7. The method of claim 6, wherein the coating further comprises a stereospecific compound.

8. The method of claim 7, wherein the stereospecific compound comprises a mixture of D isomers and L isomers.

9. The method of claim 7, wherein the stereospecific compound comprises a D isomer.

10. The method of claim 7, wherein the stereospecific compound comprises an L isomer.

11. A method of sensing an analyte, the method comprising:
    contacting a sample comprising an analyte to a metal electrode, the metal electrode comprising a coating and an overcoating, wherein the overcoating comprises a surfactant, wherein the coating comprises a sulfur containing moiety in its molecular structure, wherein
    the coating does not result in a loss of the sensing characteristics of the electrode, and wherein;
    the coating is selected from the group consisting of 2-mercaptoethanol, 2-mercaptoethylamine, 3-mercaptopropionic acid, thiophene, L-cysteine, L-cystine, D-cysteine, D-cystine, L-homocysteine, D-homocysteine, and wherein
    a temporal stability of the coated metal electrode is greater than a temporal stability of a corresponding uncoated metal electrode; and obtaining a measurement indicative of a presence of the analyte in the sample.

12. The method of claim 11, wherein the coating further comprises a stereospecific compound.

13. The method of claim 12, wherein the stereospecific compound comprises a mixture of D isomers and L isomers.

14. The method of claim 12, wherein the stereospecific compound comprises a D isomer.

15. The method of claim 12, wherein the stereospecific compound comprises an L isomer.

* * * * *